US011911087B2

(12) United States Patent
Foxall et al.

(10) Patent No.: US 11,911,087 B2
(45) Date of Patent: Feb. 27, 2024

(54) CONTROLLED SWITCHING NETWORK FOR ELECTROPHYSIOLOGY PROCEDURES

(71) Applicant: BioSig Technologies, Inc., Westport, CT (US)

(72) Inventors: Thomas G. Foxall, Surrey (CA); Budimir S. Drakulic, Los Angeles, CA (US); Sina Fakhar, Encino, CA (US); Branislav Vlajinic, Los Angeles, CA (US)

(73) Assignee: BioSig Technologies, Inc., Westport, CT (US)

( * ) Notice: Subject to any disclaimer, the term of this patent is extended or adjusted under 35 U.S.C. 154(b) by 595 days.

(21) Appl. No.: 16/987,552

(22) Filed: Aug. 7, 2020

(65) Prior Publication Data

US 2022/0039856 A1 Feb. 10, 2022

(51) Int. Cl.
*A61B 18/12* (2006.01)
*A61B 18/14* (2006.01)
*A61B 18/00* (2006.01)

(52) U.S. Cl.
CPC ...... *A61B 18/1206* (2013.01); *A61B 18/1492* (2013.01); *A61B 2018/00178* (2013.01); *A61B 2018/00577* (2013.01); *A61B 2018/00916* (2013.01)

(58) Field of Classification Search
CPC ............ A61B 18/1206; A61B 18/1492; A61B 2018/00178; A61B 2018/00577; A61B 2018/00916; A61B 2018/124; A61B 2018/1246; A61B 2018/1273; A61N 1/00; A61N 1/06; H01R 9/00; H01R 2201/12

USPC ................ 606/34, 35, 36, 37, 38, 39, 40, 41
See application file for complete search history.

(56) References Cited

U.S. PATENT DOCUMENTS

| 3,924,641 | A | 12/1975 | Weiss |
| 5,871,506 | A | 2/1999 | Mower |
| 5,931,835 | A | 8/1999 | Mackey |
| 6,141,587 | A | 10/2000 | Mower |
| 6,907,297 | B2 | 6/2005 | Wellman et al. |

(Continued)

FOREIGN PATENT DOCUMENTS

| EP | 3115011 A1 * | 1/2017 | ............ A61B 18/02 |
| EP | 3115011 A1 | 1/2017 | |
| WO | WO 2019/217317 A1 | 11/2019 | |

*Primary Examiner* — Thomas A Giuliani
(74) *Attorney, Agent, or Firm* — Sterne, Kessler, Goldstein & Fox P.L.L.C.

(57) ABSTRACT

Described herein are embodiments of a switching network for integrating electrophysiology components into an electrophysiology system. These electrophysiology components may include electrophysiology recorder, three-dimensional mapping systems, radio frequency generators, and stimulators. The switching network provides switchable connections, which allow the electrophysiology system to be reconfigured to perform different electrophysiology procedures, such as heart signal recording and mapping, cardiac ablation, or cardiac pacing. A recorder may provide control signals to the switching network to change connections between electrophysiology equipment and a catheter in a patient's heart. The electrophysiology system may control generation of biphasic pulses for use in cardiac pacing. The electrophysiology system may reconfigure the effective size the tip electrode of a split tip catheter.

12 Claims, 5 Drawing Sheets

(56) References Cited

U.S. PATENT DOCUMENTS

| | | |
|---|---|---|
| 7,907,994 B2 | 3/2011 | Stolarski et al. |
| 8,027,721 B2 | 9/2011 | Sullivan |
| 8,538,501 B2 | 9/2013 | Venkatachalam et al. |
| 10,456,057 B2 | 10/2019 | Drakulic et al. |
| 10,485,485 B1 | 11/2019 | Drakulic et al. |
| 2005/0033137 A1* | 2/2005 | Oral .................. A61B 18/1492 606/41 |
| 2016/0135878 A1 | 5/2016 | Warner et al. |
| 2016/0184028 A1* | 6/2016 | Warner ................ A61B 5/6858 600/373 |

* cited by examiner

CONTROLLED SWITCHING NETWORK FOR ELECTROPHYSIOLOGY PROCEDURES

TECHNICAL FIELD

This application generally relates to the field of switching systems for electrophysiology procedures.

BACKGROUND

Various electrophysiology procedures may be performed by passing signals through catheter electrodes in a patient's body. Electrophysiology procedures require individual or simultaneous use of various components such as data recorders, stimulators, radio frequency (RF) generators, and mapping systems. These components all require connection to the catheter electrodes, either individually or simultaneously. Some systems use a simple connection box to connect catheter electrodes to recorders, mapping systems and stimulators. Most of the existing connection boxes take an ad hoc approach to providing these connections, with each component providing different methods of connecting the other components into the system. For example, in some cases, the recorder may control which catheter electrodes are connected. In other cases, the mapping system may control which electrodes are connected. As another example, the RF generator may be connected to specific electrodes, but control of the generator operation can be performed by the recorder, mapping system, or manually. These differences in connection and control complicate the integration of components into systems. In some cases, the ad hoc connections degrade the performance of components in a system. In other cases, components must be reconfigured to perform their operations, requiring components to be disconnected and reconnected. This can unnecessarily complicate procedures as they are being performed on a patient.

BRIEF SUMMARY

Provided herein are system, apparatus, article of manufacture, and/or method embodiments, and/or combinations and sub-combinations thereof, for improving providing a switching network to incorporate components into an electrophysiology system.

Some embodiments provide a switching network with switches, a catheter connector, a three-dimensional (3D) mapping connector, a recorder connector, a control input, an electrical switching circuit, a patch connector, an ablation connector, and a stimulator connector. The ablation connector and the stimulator may be signal delivery connectors. The catheter connector and the 3D mapping connector are configured to couple a 3D mapping system to catheter electrodes. The patch connector is configured to couple a patch electrode to the ablation connector and the stimulator connector. The catheter connector, the recorder connector, and the switches are configured to couple a recorder system, catheter electrodes, and the switches to nodes. The catheter electrodes are connected to the nodes through catheter connections in the catheter connector. Each node couples a catheter connection to a switch and a recorder connection. The switches and the signal delivery connectors are configured to couple signal delivery systems, such as an ablation system or a stimulator, to the switches through the signal delivery connections. The control input and the switches are configured to couple a control input signal to the switches through the electrical switching circuit. The electrical switching circuit is configured to close switches to couple signals through the switches or open switches to decouple signals through the switches.

Some embodiments of the switching network can include an RF prefilter on a primary ablation line. This RF prefilter is coupled to the recorder connection and is configured to filter signals passing from other components connected to the primary ablation line into the recorder. Filter switches are located on each side of the RF prefilter and are configured to couple the RF prefilter into the primary ablation line when closed and to bypass the RF prefilter when opened.

Some embodiments of the switching network can include protection resistors configured to electrically protect the recorder connector from signals passing from the catheter connector and the switches.

Some embodiments of the switching network can include preamplifiers configured to amplify signals passing into the recorder connector from the nodes.

Some embodiments provide an apparatus for processing signals during an ablation procedure. The apparatus includes switches and a control circuit configured to switch the switches between two states in response to a control signal. Each switch is configured to couple a catheter to a recording system. Each switch is also configured to couple the catheter to a mapping system, an ablation generator, or a stimulator, and when in a disconnected state, to decouple the mapping system, the ablation generator, or the stimulator.

Some embodiments provide systems and methods for performing biphasic pacing of a patient's heart. A primary pulse may be determined to apply to the patient's heart that is sufficient to depolarize heart tissue and cause a heartbeat in a specific location in the patient's heart. The primary pulse may be combined with an inverse pulse into a combined pulse. The combined pulse may be applied to the patient's heart through a catheter electrode. The combined pulse may be a biphasic pulse or may be an adjusted biphasic pulse by measuring a signal level on the catheter electrode. The inverse pulse of the combined pulse is adjusted to generate a biphasic pulse based on a comparison of the signal level to a reference or baseline level. Once the biphasic pulse is determined, biphasic pacing may be performed using the biphasic pulse.

Further embodiments, features, and advantages of the present disclosure, as well as the structure and operation of the various embodiments of the present disclosure, are described in detail below with reference to the accompanying drawings.

BRIEF DESCRIPTION OF THE DRAWINGS/FIGURES

The accompanying drawings, which are incorporated herein and form a part of the specification, illustrate embodiments of the present disclosure and, together with the description, further serve to explain the principles of the disclosure and to enable a person skilled in the art(s) to make and use the embodiments.

In the drawings, like reference numbers generally indicate identical or similar elements. Additionally, generally, the left-most digit(s) of a reference number identifies the drawing in which the reference number first appears.

DETAILED DESCRIPTION

Provided herein are system, apparatus, article of manufacture, and/or method embodiments, and/or combinations and sub-combinations thereof, for improving providing a switching network to incorporate components into an electrophysiology system.

Figure 1:
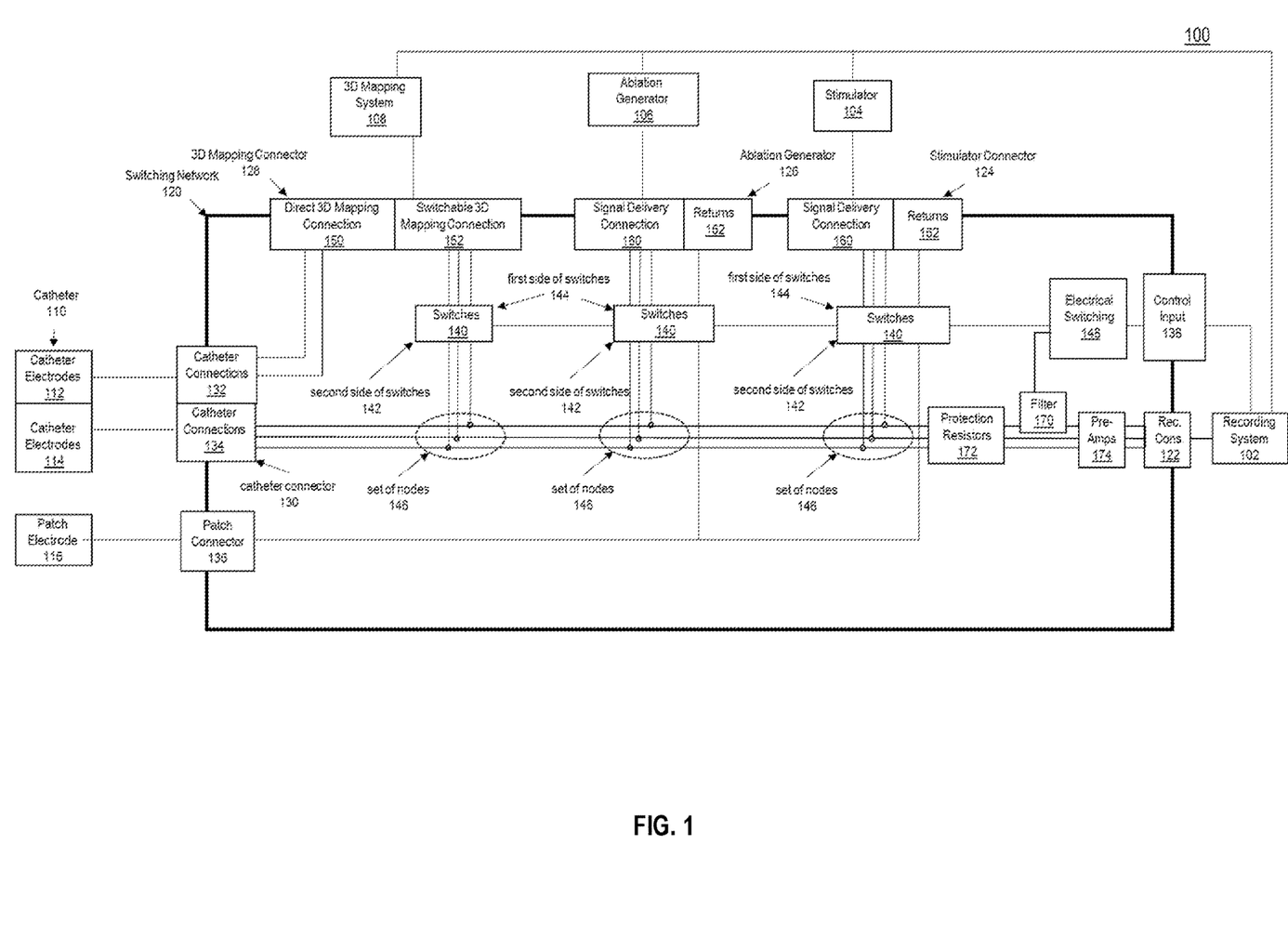
FIG. 1 illustrates a block diagram of an electrophysiology system incorporating a switching network, according to some embodiments.

FIG. 1 illustrates a block diagram of an electrophysiology system 100 incorporating a switching network 120 coupling together a recorder system 102, a stimulator 104, an ablation generator 106, a three-dimensional (3D) mapping system 108, a catheter 110, and a patch electrode 116.

The recorder system 102 is coupled to the switching network 120 by a recorder connector 122 and a control input 138. In some embodiments, the recorder system 102 receives signals from the recorder connector 122 and provides control signals to the control input 138. The recorder system 102 can be configured to record or process the signals received through the recorder connector. Control signals may be provided to the control input 138 and may be configured to change the position of switches 140 in the switching network 120. The recorder system 102 can be configured to provide control of the electrophysiology system 100 and receive signals indicating electrical activity in a heart of a patient.

In some embodiments, the recorder system 102 is configured to control one or more of the stimulator 104, the ablation generator 106, and the 3D mapping system 108. Control signals may be provided from the recorder system 102 to turn on or off the stimulator 104, the ablation generator 106, or the 3D mapping system 108. The control signals may change settings of the output for the stimulator 104 and the ablation generator 106. The control signals may change input settings for the 3D mapping system 108. The recorder system 102 may receive information from the stimulator 104, the ablation generator 106, and the 3D mapping system 108, including operational status, performance metrics, or data gathered by the 3D mapping system 108.

The stimulator 104 is coupled to the switching network 120 by a stimulator connector 124. The stimulator connector 124 has a return 162 that couples a return path from the switching network 120 to the stimulator 104. The stimulator connector 124 has signal delivery connections 160 that couple pacing sources from the stimulator 104 to the switching network 120.

In some embodiments, the stimulator 104 is configured to provide pacing. The stimulator 104 can be configured to generate pulses with specific waveforms for pacing, as would become apparent to persons of ordinary skill in the art. The pulses may be monophasic or biphasic. The stimulator 104 can be configured to provide monophasic or biphasic pacing.

The ablation generator 106 is coupled to the switching network 120 by an ablation connector 126. The ablation connector 126 has a return 162 that couples a return path from the switching network 120 to the ablation generator 106. The ablation connector 126 has signal delivery connections 160 that couple ablation sources from the ablation generator 106 to the switching network 120. In some embodiments, the ablation generator 106 is configured to provide ablation signals for cardiac ablation, as would become apparent to persons of ordinary skill in the art.

The 3D mapping system 108 is coupled to the switching network 120 by a 3D mapping connector 128. In some embodiments, the 3D mapping system 108 is configured to perform 3D mapping of a heart of a patient based on received signals from a catheter 110 located in the heart, as would become apparent to persons of ordinary skill in the art.

In some embodiments, the catheter 110 has a first set of catheter electrodes 112 and a second set of catheter electrodes 114. The catheter 110 can be configured to be inserted into the heart of a patient to measure electrical signals from the heart, as would become apparent to persons of ordinary skill in the art. The catheter 110 is coupled to the switching network 120 by catheter connector 130. Catheter connector 130 comprises a first set of catheter connections 132 and a second set of catheter connections 134. The first set of catheter connections 132 are coupled to the first set of catheter electrodes 112. The second set of catheter connections 134 are coupled to the second set of catheter electrodes 114.

The patch electrode 116 is coupled to the patch connector 136. The patch electrode 116 can be configured to provide a return path to the switching network 120 from an external connection to the patient.

The switching network 120 can include the recorder connector 122, the stimulator connector 124, the ablation connector 126, the 3D mapping connector 128, the catheter connector 130, the patch connector 136, the control input 138, the switches 140, the electrical switching circuit 148, a filter 170, protection resistors 172, and preamplifiers 174.

In some embodiments, each of the switches 140 in the switching network 120 are a single type of switch. In other embodiments, the switches 140 in the switching network 120 may be different types of switches. For example, some of the switches 140 may be mechanical switches and other of the switches 140 may be transistor switches The control input 138 is coupled to the switching circuit 148. The switching circuit 148 is coupled to the switches 140. In some embodiments, the switching circuit 148 is connected to the filter 170. The switching circuit 148 can be configured to change the position of switches 140 or filter switches in the filter 170. In some embodiments, the switches 140 can be mechanical devices, transistors or other digital switches, as would become apparent to persons of ordinary skill in the art.

The signal delivery connections 160 of the stimulator connector 124 and the ablation connector 126 are coupled to the switches 140 at a first side of switches 144. The returns 162 of the stimulator connector 124 and the ablation connector 126 can be coupled to the switches 140 at the first side of the switches 144.

Those skilled in the art will appreciate that while signal delivery connections 160 and returns 162 may perform a similar function for the stimulator connector 124 and the ablation connector 126, the signal delivery connections 160 and returns 162 may be different for the different connectors.

The 3D mapping connector 128 can have a direct 3D mapping connection 150, which is coupled to the catheter connector 130 at a first set of catheter connections 132. The 3D mapping connector 128 can have a switchable 3D mapping connection 152 that is coupled to the switches 140 at the first side of the switches 144.

The switches 140 have a second side of switches 142. The signal delivery connections 160 coupled to the first side of switches 144 are coupled through the switches 140 to the second side of switches 142 and then to a set of nodes 146. The set of nodes 146 are coupled to the recorder connector 122 and the catheter connector 130 at a second set of catheter connections 134. Returns 162 coupled to the first side of switches 144 are coupled through the switches 140 to the second side of switches 142 and then to the patch connector 136.

In some embodiments, the filter 170 is coupled between the set of nodes 146 and the recorder connector 122. The protection resistors 172 can be coupled between the set of nodes 146 and the recorder connector 122. The preamplifiers 174 can be coupled between the set of nodes 146 and the recorder connector 122.

The switching network 120 is configured to connect the various components through the connectors, as described above, and provide switching through the switches 140 to configure the connections between the components to perform electrophysiology procedures. Operation of the electrophysiology system 100 is improved by the switching network 120, which provides a single component for coupling the various electrophysiology systems together. This minimizes unnecessary direct connections to the catheter electrodes, thus eliminating loading and interference from unused equipment. The switches 140 allow each component to be connected to the electrodes in the catheter 110 only as necessary. The control input 138 allows for control of the switches to come from a single system, such as the recording system 102, for example.

The switching network 120 allows for improved stimulation or pacing. The switches 140 allow for a switchable stimulator input from the stimulator 104. By switching the connections between the stimulator 104 and the catheter 110, the electrophysiology system 100 can determine which electrodes in the catheter 110 have the best contact with the heart tissue, for example. In some embodiments, the best contact for the electrodes in the catheter 110 can be determined by the recorder system 102 by monitoring changes in the morphology of the recorded signal as cardiac tissue is contacted. Pacing can be performed through these electrodes to improve effectiveness.

The switches 140 allow for connections in the switching network 120 to be changed to provide pacing and ablation individually, or in combination with sensing.

Further, the switching network 120 allows for feedback of information from the recorder system 102 to other components in the electrophysiology system 100. In an embodiment, the recorder system 102 can be implemented using an electrophysiology signal acquisition, digital signal processing, and analysis system such as PureEP™, manufactured by BioSig Technologies, Inc., Westport, Conn., which is disclosed in U.S. Pat. No. 10,356,001 and is incorporated herein by reference. For example, during pacing, physicians may want to see local activity in the cardiac tissue as soon as possible after the pacing pulse. Since pacing pulses are very large relative to the signals of interest (volts vs mV), the pulses tend to saturate the input stages. Attempts to display measured for observation in existing systems are not effective because the signal does not return to baseline for tens or hundreds of milliseconds. The electrophysiology system 100, using the switching network 120, can adjust the magnitude and duration of the pacing signal to reduce the signal return to baseline time to a few milliseconds or less.

As another example, in RF ablation, diagnostic systems, which may be located in the recorder system 102, can optimize the ablation energy by monitoring the effectiveness of the ablation power and adjusting it as necessary.

As a further example, when performing processes that might damage other components in the electrophysiology system 100, the switching network 120 can change the positions of switches 140 to protect the components from those processes.

The switching network 120 advantageously allows components to be disconnected by the switches 140 during 3D mapping to improve sensitivity and reduce interference. In some embodiments, the 3D mapping system 108 is always connected to the catheter.

Figure 2:
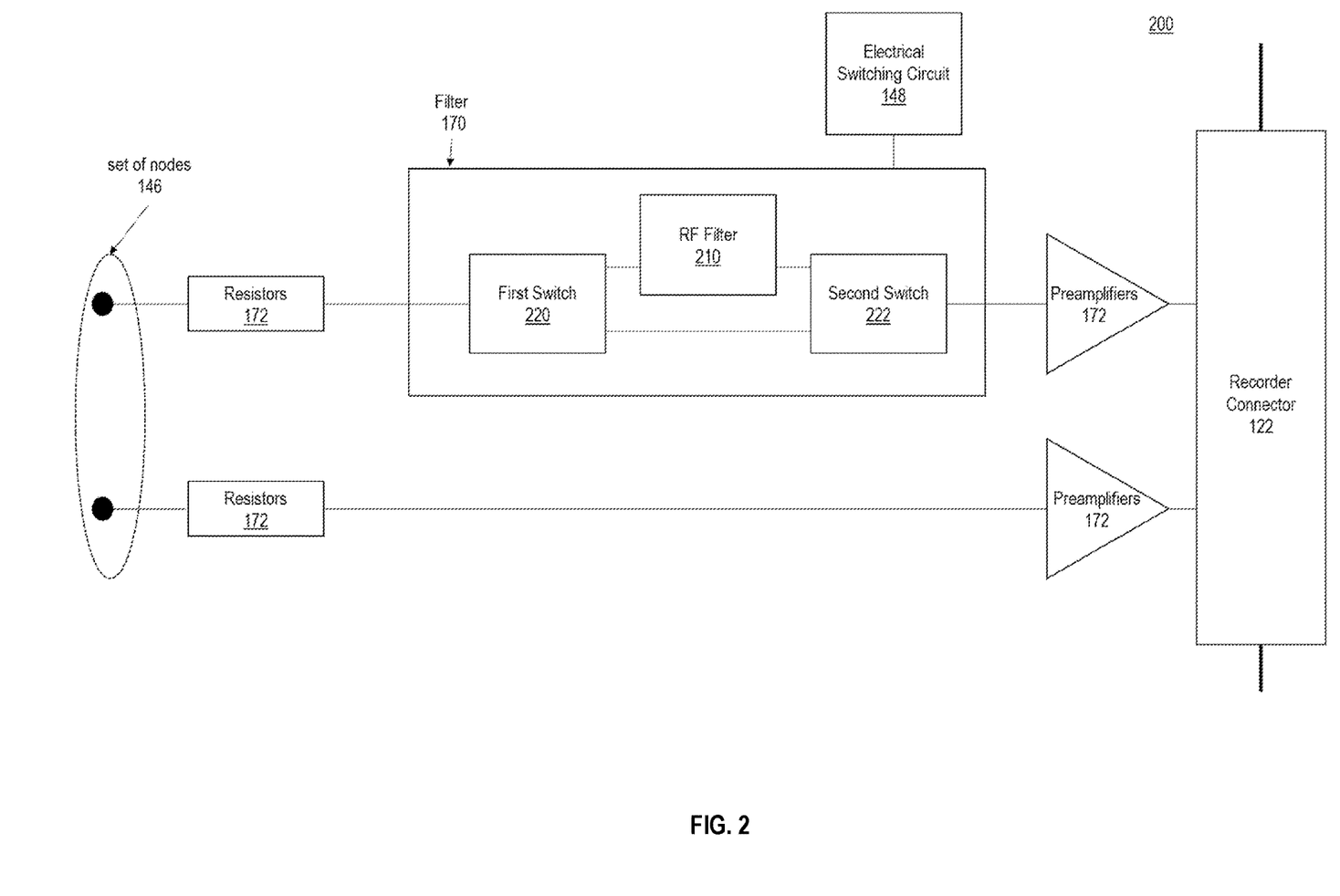
FIG. 2 illustrates a portion of the controlled switching network, according to some embodiments.

FIG. 2 illustrates a portion 200 of the controlled switching network 120. This portion 200 shows the recorder connector 122, the set of nodes 146, the electrical switching circuit 148, the filter 170, the protection resistors 172, and the preamplifiers 174. The filter 170 has a first switch 220, a second switch 222, and an RF filter 210.

The RF filter 210 is configured to attenuate signals. In some embodiments, it attenuates signals during ablation. It can attenuate signals with frequencies above 300 kHz. Referring back to the electrophysiology system 100 from FIG. 1, the RF filter 210 can be in addition to other filtering in the recorder system 102. The RF filter 210 can improve noise and allow improved viewing of cardiac signals by the recorder system 102 during ablation procedures.

The first switch 220 and the second switch 222 are configured to, in one position, couple the RF filter 210 between the set of nodes 146 and the recorder connector 122. The first switch 220 and the second switch 222 are configured to, in a second position, bypass the RF filter 210 so that it is not coupled and signals passing into the recorder connector from the set of nodes 146 are not attenuated by the RF filter 210. The electrical switching circuit 148 can be configured to provide signals to change the positions of the first switch 220 and the second switch 222.

In some embodiments, the filter 170 is coupled on a primary ablation line. The RF filter 210 can be coupled into the system as described above when the electrophysiology system 100 is performing ablation. The RF filter 210 can be decoupled from the system as described above when the electrophysiology system 100 is performing other functions, such as 3D mapping, stimulation, or analysis.

In some embodiments, the resistors 172 are configured to limit current that flows to the recorder connector 122. This current limiting may protect the recorder system 102 (not shown in FIG. 2) when the electrophysiology system 100 is performing defibrillation. The resistors 172 can be coupled between the set of nodes 146 and the filter 170. The resistors may be coupled between the set of nodes 146 and the preamplifiers 174.

In some embodiments, the preamplifiers 174 are configured to improve noise performance in the electrophysiology system 100. This may be accomplished by locating the preamplifiers 174 between the filter 170 and the recorder connector 122. The preamplifiers 174 can be located between the resistors 172 and the recorder connector 122. The placement of the preamplifiers 174 in the switching network 120 can minimize noise or other interference in the electrophysiology environment.

Figure 3:
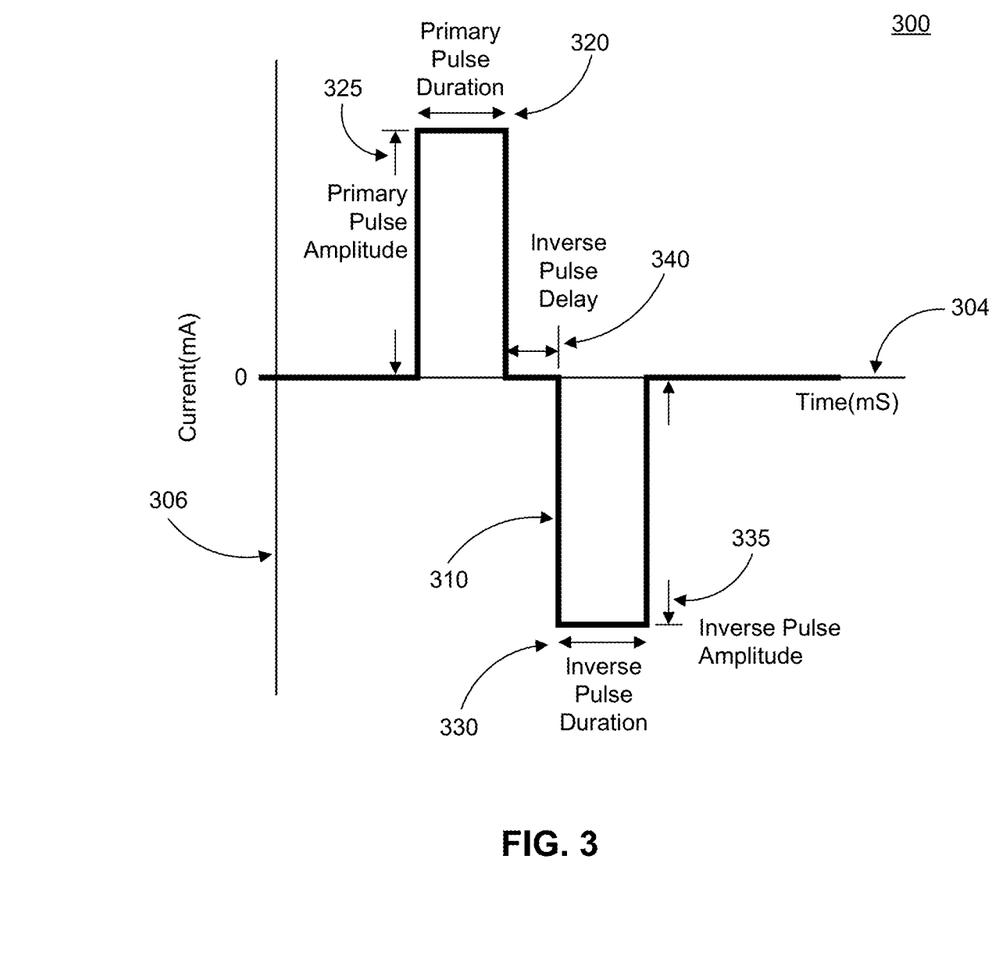
FIG. 3 illustrates a biphasic pulse for use in electrophysiology studies, according to some embodiments.

FIG. 3 illustrates a biphasic pulse 310 for use in stimulation or pacing. The graph 300 has an x-axis 304 depicting time in milliseconds and a y-axis 306 depicting current in milliamps. The biphasic pulse 310 has primary pulse with a primary pulse duration 320 and a primary pulse amplitude 325 and an inverse pulse with an inverse pulse duration 330 and an inverse pulse amplitude 335. The primary pulse is separated from the inverse pulse by an inverse pulse delay 340.

In some embodiments, the stimulator 104 can be a programmable current source configured for performing stimulation or pacing, including monophasic, biphasic, cathodal, or anodal pacing. The recorder system 102 can be configured to control the switching network 120 to select the stimulator output locations and polarity.

In some embodiments, the electrophysiology system 100 can be configured to determine an electrode in the catheter 110 that has best contact with heart tissue of the patient. Pacing may be controlled to pace through that electrode. The patch electrode 116 can be connected and configured to be a stimulator output to enable unipolar pacing. The electrophysiology system 100 can configure the switching network to maintain capture of the pacing threshold based on input received by the recording system 102.

In some embodiments, the stimulator 104 provides biphasic pacing, which may bring the lead signal back to a baseline and allow the recorder system 102 to capture local activity around the catheter more quickly than with a monophasic pulse. Biphasic pacing may be accomplished by accurate monitoring of the lead and control lines by the recorder system 102, which in turn may correct the level and interval of the inverse pulse and offset saturation and recovery from the primary pulse.

Figure 4:
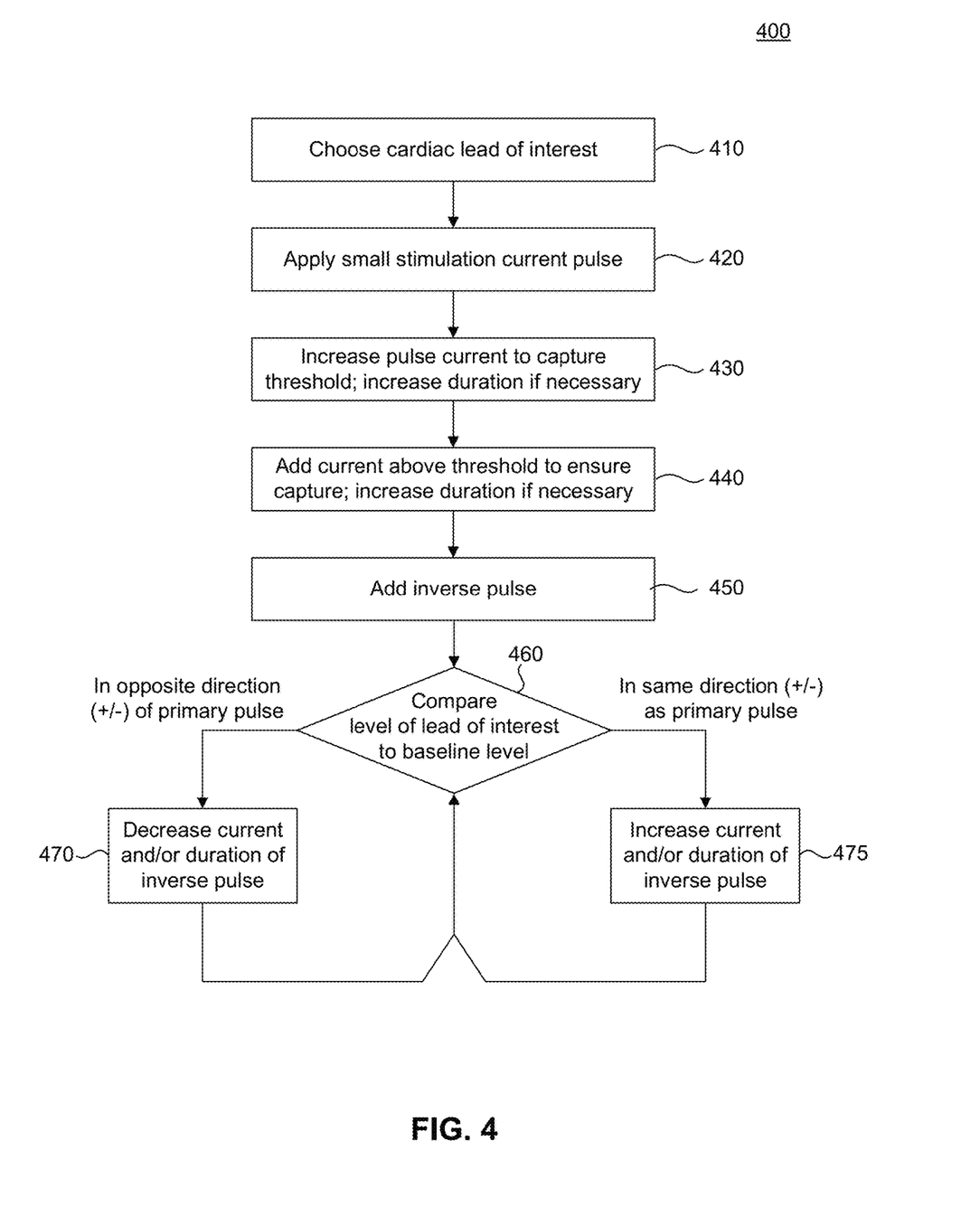
FIG. 4 is a flow chart illustrating a method for generating a biphasic pulse, according to some embodiments.

FIG. 4 is a flow chart illustrating a method 400 for generating a biphasic pulse 310. The biphasic pulse 310 can be generated by the stimulator 104 using method 400. The stimulator 104 can be controlled by the recorder system 102 to generate the biphasic pulse 310.

In 410, a cardiac lead of interest is chosen. This cardiac lead may be chosen based on a location in the patient's heart where pacing is to be performed. The recorder system 102 can be configured identify the cardiac lead of interest. The recorder system 102 can be configured to provide control signals to the switching network 120 to configure the switches to connect the stimulator 104 to the cardiac lead of interest in the catheter 110. In some embodiments, the cardiac lead is chose based on being on a location below the top of the patient's heart. Step 410 may select a lead in catheter 110 on which to apply a biphasic pulse.

In 420, a programmable stimulation current pulse is applied to a patient's heart. The stimulation pulse may be generated by the stimulator 104 and provided to the heart through the catheter 110 and may be monitored by recording system 102.

In 430, the pulse current is increased to determine the capture threshold. Step 420 can also increase the duration of the pulse current if necessary. Determining the capture threshold may mean increasing the pulse current of the primary pulse, the duration of the primary pulse, or both, such that a primary pulse creates a signal that envelopes a signal necessary to cause depolarization of heart tissue. The depolarization of the heat tissue may be sufficient to cause a heartbeat at a location in the patient's heart that is in contact with a catheter electrode. In some embodiments, the capture threshold is based at least in part on the specific cardiac lead of interest chosen in step 410 or the point of contact on the heart made by the specific cardiac lead of interest.

In some embodiments, the increase of the current may be an increase of the primary pulse amplitude 325, the primary pulse duration 320, or both. The increase in duration or amplitude may be an amount sufficient to identify the threshold necessary to affect a change in heart pacing. The recorder system 102 can control the stimulator 104 to adjust the amplitude and duration levels.

In 440, current is added above the threshold to ensure capture. Step 440 can also increase the duration if necessary. These additional increases in the primary pulse amplitude 325 and primary pulse duration 320 can ensure that the heart tissue is depolarized at the pacing electrode location and that the pacing signal affects the patient's heart. The resulting pulse may be a primary pulse, as described in FIG. 3 above for the biphasic pulse 310.

In some embodiments, the additional current, duration, or both, are added in step 440 to create a primary pulse that is shaped to ensure that the threshold signal can be captured in the envelope of the primary pulse.

In 450, an inverse pulse is added to the primary pulse. This inverse pulse may have an inverse pulse amplitude 335 and an inverse pulse duration 330 that are the same as the primary pulse amplitude 325 and the primary pulse duration 320. The inverse pulse may be delayed from the primary pulse by an inverse pulse delay 340. The addition of the inverse pulse may create a biphasic pulse. The inverse pulse may be generated by the stimulator 104.

Step 450 can add an inverse pulse to the primary pulse to create a biphasic pulse. This pulse may be applied to the patient's heart through catheter 110 to depolarize the patient's heart.

In 460, the level of the lead of interest is compared to a baseline level or isoelectric line. The isoelectric line is a signal level at which the recorder system 102 can monitor signals, such as signals from the patient's heart. The baseline level may be a level with a current amplitude of zero or approximately zero.

The comparison to the isoelectric line level may determine if the level of the lead of interest is in the same or opposite direction of the primary pulse. The recorder system 102 can be configured to compare the level the lead to the isoelectric line.

If the level of the lead of interest is in the opposite direction of the primary pulse, method 400 proceeds to step 470 and decreases the current, the duration, or both, of the inverse pulse.

If the level of the lead of interest is in the same direction of the primary pulse, method 400 proceeds to step 475 and increases the current, the duration, or both, of the inverse pulse.

After step 470 or 475, method 400 returns to step 460 and repeats the adjustment of the biphasic pulse.

As an example of how method 400 works, a patient's heart may need a certain signal level and duration to depolarize heart tissue and cause the patient's heart to beat. Biphasic pacing, as described herein, may be performed on the patient's heart through a catheter 110 in the patient's heart at the lead chosen in step 410. An electrophysiology system 100 can apply steps 420, 430, and 440 to generate a primary pulse that envelopes the certain signal level. Enveloping the certain level means that the amplitude and duration of the primary pulse are set to exceed the certain signal level. Accordingly, the primary pulse is sufficient to, when applied to the patient's heart, cause depolarization of heart tissue and a heart beat in the patient's heart.

When a pacing signal is applied to a patient's heart, the pacing signal in the heart must return to baseline before signals from the patient's heart may be monitored without interference. If a single-sided pulse is applied, signal levels in the patient's heart must return to the baseline on their own, which can take tens or hundreds of milliseconds. By applying the biphasic pulse, the inverse signal can drive the signal levels back to baseline faster, within a few milliseconds. This allows monitoring of signals sooner.

In some embodiments, the additional of the inverse pulse alone to form the biphasic pulse is insufficient to drive the signal level to the baseline. This may be due to a variety of reasons, including signal noise or degradation, signal propagation through the patient's heart, or other reasons. Steps 460 accounts for variation in the effectiveness of the inverse pulse by comparing the signal level to the baseline. If the signal level is in the direction of the primary pulse from the baseline, the inverse pulse has overdriven the signal level past the baseline and step 470 decreases the signal current, duration, or both, so that the next time the pulse is applied, the signal level returns closer to the baseline. If the signal level is in the opposite direction of the primary pulse from the baseline, the inverse pulse has not driven the signal level to the baseline sufficiently and step 475 increases the signal current, duration, or both, so that the next time the pulse is applied, the signal level returns closer to the baseline. Method 400 can then return to step 460 to continue adjusting the inverse signal in the biphasic pulse.

In some embodiments, method 400 modifies the biphasic pulse to form a corrected biphasic pulse, which more effectively causes the signal level to return to baseline.

In some embodiments, method 400 continues to modify the biphasic pulse throughout performing biphasic pacing.

The biphasic pacing may be performed on a patient's heart by determining a primary pulse to apply to the patient's heart sufficient to depolarize heart tissue and cause a heartbeat in a first location in the patient's heart and combining the primary pulse with an inverse pulse into a combined pulse. The pulse may then be applied to the patient's heart through a catheter electrode. The signal level may be measured or monitored after the application of the combined pulse on the catheter electrode and the inverse pulse may be adjusted to generate a biphasic pulse. The adjusting may be based on a comparison of the signal level to a reference level. Once the pulse is generated, biphasic pacing may be performed using the biphasic pulse.

Biphasic pacing may further include continually adjusting the inverse pulse in the biphasic pulse based on the comparison of the signal level to the reference level after each respective biphasic pulse is applied during the performing of biphasic pacing.

In some embodiments, the primary pulse may be determined by applying an initial electrical pulse configured to be insufficient to envelope a pacing threshold and incrementally increasing the initial electrical pulse to determine the primary pulse that will envelope the pacing threshold. The primary pulse and the inverse pulse may be initially set to have the same current amplitude and duration, but the inverse pulse has a current amplitude with an opposite sign. The inverse pulse maybe be applied with a slight delay from the primary pulse.

Adjusting the level of the inverse pulse may be in response to the inverse pulse resulting a signal level in the same direction as the primary pulse from the baseline or the opposite direction as the primary pulse from the baseline. For example, when the inverse pulse results in a signal level below the signal baseline, the inverse pulse may be adjusted by reducing the current amplitude of the inverse pulse, the duration of the inverse pulse, or both. When the inverse pulse results in a signal level above the signal baseline, the inverse pulse may be adjusted by increasing the current amplitude of the inverse pulse, the duration of the inverse pulse, or both.

Figure 5A:
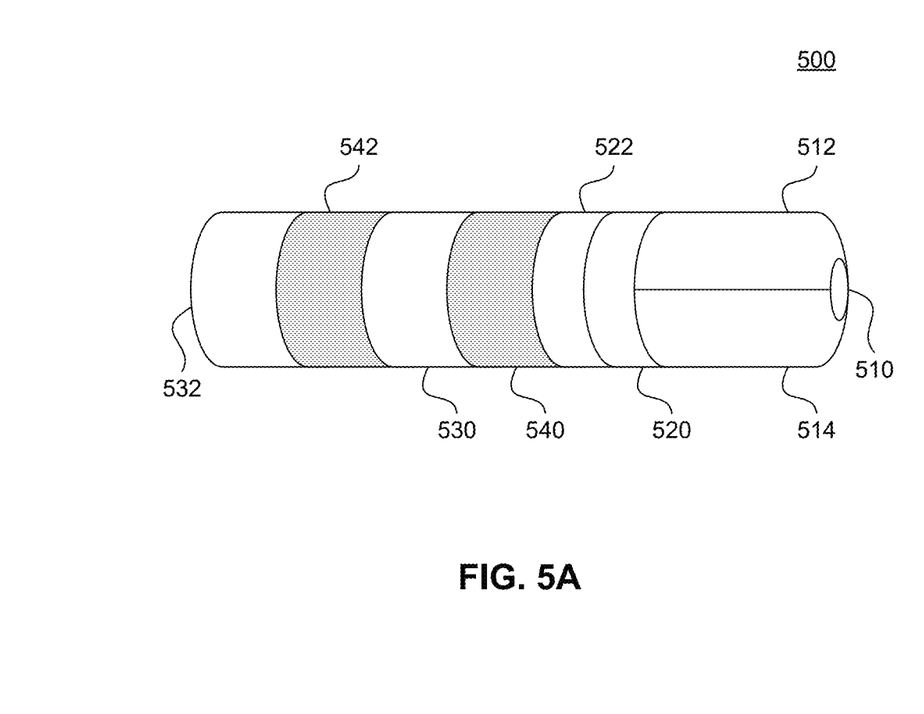
FIG. 5A illustrates a split-tip catheter, according to some embodiments.

FIG. 5A illustrates a split-tip catheter 500, according to another invention disclosed herein. The split-tip catheter has tip (distal) electrodes 510, 512, 514, and 516 (516 is not shown in FIG. 5A, as it is out of view), 520 and 522, ring electrodes 530 and 532, and spacing portions 540 and 542 ("spacers").

Figure 5B:
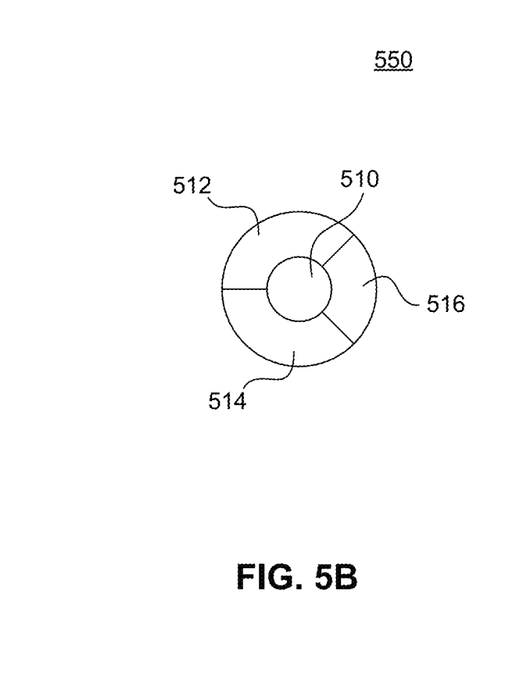
FIG. 5B illustrates the distal electrode of a split-tip catheter, according to some embodiments.

FIG. 5B illustrates an end-view 550 of the split-tip catheter 500, which shows the tip electrodes 510, 512, 514, and 516. Each electrode (e.g., 510, 512, 514, 516, 520, 522, 530 and 532) is configured to be exposed to the intracardiac surface of a patient, but not necessarily at the same time depending on the orientation of the catheter 500.

The split-tip catheter 500 includes insulated wires coupled to each electrode (e.g., 510, 512, 514, 516, 520 522, 530 and 532) for connection to a system as discussed further below. The electrodes (510, 512, 514, 516, 520, 522, 530 and 532) can be formed of an electrically conductive material, such as a noble metal, or alloys, or combinations thereof, as would be apparent to a person skilled in the art. The body and spacers of the catheter 500 can be formed of a thermoplastic elastomer material, woven Dacron, or other synthetic materials, such as polyurethane, as would be apparent to a person skilled in the art.

The split-tip catheter 500 can be used as a catheter in the electrophysiology procedures discussed above. In general, mapping is done more accurately using small electrodes, which provide more spatial detail in mapping heart activity. Pacing is also more effective using small electrodes, which produce a higher current density at the point of contact for more effective capture and spatial resolution. Ablation, on the other hand, is generally more efficient using a large electrode, which provides better contact over a larger area to dissipate heat more evenly and efficiently. The tip electrodes 510, 512, 514, 516, 520 and 522, can be configured by the switching network 120 to make a variable sized electrode by combining segments to optimize the effective size for different operations. The ring electrodes 530 and 532 can be used for bipolar or unipolar sensing as applicable for conventional catheters.

The tip of the split-tip catheter 500 is split into two or more split-tip electrodes, such as electrodes 512 and 514. For example, as shown in FIGS. 5A and 5B, the tip may be split into five electrodes 512, 514, 516, 520, and 522 as a split-tip. Electrodes 512, 514, and 516 in the split-tip can be the same size and equally spaced around the end of the split-tip catheter 500, but may have unequal sizes.

As depicted in FIG. 5, the tip electrode 510 can be located on the end of the catheter 500, but need not entirely cover the end. The split-tip electrodes 512, 514, and 516 can be spaced equidistance, circumferentially around the end of the catheter 500.

This disclosed split-tip design improves over existing catheters with a single electrode on the end because the electrodes may be switched on or off based on their contact with the heart. Turning on electrodes that are not in contact with the heart may cause coagulation of blood around the heart, which is not good for a patient. It may also result in inefficient power consumption in generating ablation or pacing signals. By splitting the tip, only the electrodes in good electrical contact with the heart need be turned on. In addition, the effective size of the tip electrode can be changed in real time to optimize RF power delivery to the cardiac tissue during ablation.

In some embodiments, the split-tip catheter 500 can be connected to the switching network 120 in the electrophysiology system 100. The tip electrode 510 and split-tip electrodes 512, 514, 516, 520, and 522 can be coupled to the recorder system 102 such that they can be monitored to determine which of them is in contact with a location on the heart to be ablated. Once the electrodes in contact with the heart are determined, the switching network 120 can switch the electrophysiology system 100 in to ablation mode and switch the ablation generator 126 to provide ablation signals to the electrodes that are in contact with the heart.

For example, if split-tip electrodes 512 and 514 are determined to be in contact with the heart, the switching network 120 can switch the connections between the ablation generator 126 and the catheter 500 to only ablate on those electrodes. This advantageously may reduce noise and improve unipolar signal quality.

For sensing applications, such as 3D mapping, having separate electrodes in close proximity on the tip of the catheter allows for reduction of far field effects. In some conventional systems, far field effects add significant noise and reduce signal quality. The split-tip design allows monitoring at multiple locations in close proximity to the area of interest. The signals can be averaged to determine the far field effect, which may then be subtracted from the measured signal, reducing the interference.

In some embodiments, the split-tip catheter has a distal end with two or more electrodes spaced circumferentially around the distal end, the electrodes extending from part of the tip of the distal end onto the body of the catheter. The body of the catheter, which extends between the distal and proximal ends, may have one or more circumferential electrodes located on it. These circumferential electrodes extend around the circumference of the catheter body.

In some embodiments, the distal end of the catheter also has an electrode located on the tip of the distal end. This electrode may be proximately located to the electrodes on the distal end such that each proximately located electrode is in contact with the electrode on the tip.

In some embodiments, the proximal end of the split-tip catheter has connections for coupling to a source or measuring device, such as a 3D mapping system, a recorder, or an ablation generator. The catheter may be configured to provide electrical signals from the connections to electrodes located on the catheter or to measure signals at the electrodes and provide them to external equipment through the connections.

The electrodes on the body of the catheter may be of different sizes. For example, there may be first one or more electrodes and second one or more electrodes, where the first one or more electrodes are shorter, measuring from the distal to proximal ends of the catheter, than the second one or more electrodes. The first one or more electrodes may be located proximally to the electrodes spaced around the distal end of the catheter, while the second one or more electrodes may be located between the first one or more electrodes and the proximal end. In some embodiments, there may be spacing portions along the length of the catheter between any or each of the first and second one or more electrodes. These spacing portions may be non-conductive.

It is to be appreciated that the Detailed Description section, and not any other section, is intended to be used to interpret the claims. Other sections can set forth one or more but not all exemplary embodiments as contemplated by the inventor(s), and thus, are not intended to limit this disclosure or the appended claims in any way.

While this disclosure describes exemplary embodiments for exemplary fields and applications, it should be understood that the disclosure is not limited thereto. Other embodiments and modifications thereto are possible, and are within the scope and spirit of this disclosure. For example, and without limiting the generality of this paragraph, embodiments are not limited to the software, hardware, firmware, and/or entities illustrated in the figures and/or described herein. Further, embodiments (whether or not explicitly described herein) have significant utility to fields and applications beyond the examples described herein.

Embodiments have been described herein with the aid of functional building blocks illustrating the implementation of specified functions and relationships thereof. The boundaries of these functional building blocks have been arbitrarily defined herein for the convenience of the description. Alternate boundaries can be defined as long as the specified functions and relationships (or equivalents thereof) are appropriately performed. In addition, alternative embodiments can perform functional blocks, steps, operations, methods, etc. using orderings different from those described herein.

References herein to "one embodiment," "an embodiment," "an example embodiment," "some embodiments," or similar phrases, indicate that the embodiment described can include a particular feature, structure, or characteristic, but every embodiment can not necessarily include the particular feature, structure, or characteristic. Moreover, such phrases are not necessarily referring to the same embodiment. Further, when a particular feature, structure, or characteristic is described in connection with an embodiment, it would be within the knowledge of persons skilled in the relevant art(s) to incorporate such feature, structure, or characteristic into other embodiments whether or not explicitly mentioned or described herein.

Additionally, some embodiments can be described using the expression "coupled" and "connected" along with their derivatives. These terms are not necessarily intended as synonyms for each other. For example, some embodiments can be described using the terms "connected" and/or "coupled" to indicate that two or more elements are in direct physical or electrical contact with each other. The term "coupled," however, can also mean that two or more elements are not in direct contact with each other, but yet still co-operate or interact with each other.

The breadth and scope of this disclosure should not be limited by any of the above-described exemplary embodiments, but should be defined only in accordance with the following claims and their equivalents

What is claimed is:

1. A switching network, comprising:
a plurality of switches that each comprise a respective first side and a respective second side;
a catheter connector comprising a first set of connections and a second set of connections;
a three-dimensional (3D) mapping connector;
a recorder connector;
a control input;
an electrical switching circuit;
a patch connector;
one or more signal delivery connectors chosen from the group of: an ablation connector and a stimulator connector, wherein each of the one or more signal delivery connectors comprises a signal delivery connection and a return connection; and wherein:
the catheter connector and the 3D mapping connector are configured to couple a 3D mapping system to a first set of catheter electrodes through the first set of connections;
the patch connector and the one or more signal delivery connectors are configured to couple a patch electrode to a return of each of the one or more signal delivery connectors through the return connection of each of the one or more signal delivery connectors;

the catheter connector, the recorder connector, and the plurality of switches are configured to couple a recorder system, a second set of catheter electrodes, and the first side of each switch of the plurality of switches to a set of nodes, the second set of catheter electrodes being connected to the set of nodes through the second set of catheter connections, wherein a first node of the set of nodes is coupled to a first catheter connection of the second set of catheter connections, the first side of a first switch of the plurality of switches, and a first recorder connection of the recorder connector;

the plurality of switches and the one or more signal delivery connectors are configured to couple one or more signal delivery systems to the second side of each of the switches through the signal delivery connections, wherein the one or more signal delivery systems are chosen, based on the one or more signal delivery connectors, from the group of: an ablation generator and a stimulator; and the control input and the switches are configured to couple a control input signal to the switches through the electrical switching circuit, wherein the electrical switching circuit is configured to:
  in response to the control input signal indicating to close first one or more switches of the plurality of switches, couple the first side to the second side for each switch of the first one or more switches; and
  in response to the control input signal indicating to open second one or more switches of the plurality of switches, decouple the first side from the second side for each switch of the second one or more switches;

a first filter switch coupled to a primary ablation node of the set of nodes; and a second filter switch coupled to a primary ablation connection of the recorder connector;

wherein the control input, the first filter switch, and the second filter switch are configured to couple a filtering control input signal to the first filter switch and the second filter switch through the electrical switching circuit, wherein the electrical switching circuit is further configured to:
  in response to the filtering control input signal indicating a first state, switch the first filter switch and the second filter switch into the first state, the first state configured to couple the first filter switch to a first connection of an RF prefilter and the second filter switch to a second connection of the RF prefilter; and
  in response to the filtering control input signal indicating a second state, switch the first filter switch and the second filter switch into the second state, the second state configured to:
    decouple the RF prefilter from the primary ablation node and the primary ablation connection; and
    couple the first filter switch to the second filter switch.

2. The switching network of claim 1, wherein the RF prefilter is coupled between the primary ablation node of the set of nodes and the primary ablation connection of the recorder connector.

3. The switching network of claim 1, further comprising protection resistors configured to electrically protect the recorder connector from signals passing from the catheter connector and the switches.

4. The switching network of claim 1, further comprising preamplifiers configured to amplify signals passing into the recorder connector from the set of nodes.

5. The switching network of claim 1, further comprising a return switch, wherein:
the catheter connector further comprises a return catheter connection; and
the control input and the return switch are configured to couple a first control input signal to the return switch through the electrical switching circuit, wherein the electrical switching circuit is further configured to:
  in response to the first control input signal indicating a first state, switch the return switch to the first state, the first state being configured to decouple the patch electrode from the return and couple a catheter return electrode to the return through the return catheter connection, the return switch, and the return connection; and
  in response to the first control input signal indicating a second state, switch the return switch to the second state, the second state being configured to decouple the catheter return electrode from the return and couple the patch electrode to the return through the return switch and the return connection.

6. The switching network of claim 1, further comprising a return switch, wherein the control input and the return switch are configured to couple a first control input signal to the return switch through the electrical switching circuit, wherein the electrical switching circuit is further configured to:
  in response to the first control input signal indicating a first state, switch the return switch to the first state, the first state being configured to decouple the patch electrode from the return; and
  in response to the first control input signal indicating a second state, switch the return switch to the second state, the second state being configured couple the patch electrode to the return through the return switch and the return connection.

7. A system for processing signals during an ablation procedure, comprising: a switching network that comprises: a plurality of switches; a filter comprising: a first filter switch coupled to a filtering control input signal and a primary ablation node that couples to at least one catheter electrode of a catheter; and a second filter switch coupled to the filtering control input signal and a primary ablation connection of a recorder connector; an electrical switching circuit configured to: in response to the filtering control input signal indicating a first state, switch the first filter switch and the second filter switch into the first state which couples the first filter switch to a first connection of an RF prefilter and the second filter switch to a second connection of the RF prefilter; and in response to the filtering control input signal indicating a second state, switch the first filter switch and the second filter switch into the second state which decouples the RF prefilter from the primary ablation node and couples the first filter switch to the second filter switch; and a control circuit configured to switch each of the plurality of switches between the first state and the second state in response to a control signal; wherein each switch of the plurality of switches is configured to: couple the catheter to a recording system; couple, when in the first state, the catheter to one or more devices selected from a group consisting of: a mapping system, an ablation generator, and a stimulator; and decouple, when in the second state, the catheter from the one or more devices.

8. The system of claim 7, wherein the RF prefilter is configured to filter signals passing from at least one switch of the plurality of switches and the catheter to the recording system.

9. The system of claim 7, further comprising a plurality of protection resistors configured to electrically protect the recording system from signals from the catheter and the plurality of switches.

10. The system of claim 7, further comprising preamplifiers configured to amplify signals passing into the recording system from the catheter and the plurality of switches.

11. The system of claim 7, further comprising at least one return switch and a patch return, the at least one return switch configured to either couple a return of the one or more devices to the patch return or couple the catheter to the return of the one or more devices.

12. The system of claim 7, further comprising at least one return switch and a patch return, the at least one return switch configured to either couple a return of the one or more devices to the patch return or decouple the return of the one or more devices to the patch return.

\* \* \* \* \*